United States Patent
Makker et al.

(10) Patent No.: US 6,245,106 B1
(45) Date of Patent: Jun. 12, 2001

(54) INTRAOCULAR LENSES MADE FROM POLYMERIC COMPOSITIONS AND MONOMERS USEFUL IN SAID COMPOSITIONS

(75) Inventors: Harish C. Makker, Mission Viejo; Xiugao Liao, Irvine; Joseph I. Weinschenk, III, Laguna Niguel, all of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/286,356

(22) Filed: Apr. 5, 1999

Related U.S. Application Data
(60) Provisional application No. 60/106,381, filed on Oct. 29, 1998.

(51) Int. Cl.$^7$ ............................................... A61F 2/14
(52) U.S. Cl. ............................................... 623/5.16
(58) Field of Search ................... 623/4.1, 5.11–5.16, 623/6.11–6.17, 6.56

(56) References Cited

U.S. PATENT DOCUMENTS

| | | |
|---|---|---|
| Re. 36,150 | 3/1999 | Gupta . |
| 4,834,750 | 5/1989 | Gupta . |
| 5,290,892 | 3/1994 | Namdaran et al. . |
| 5,331,073 * | 7/1994 | Weinschenk, III et al. ......... 526/264 |
| 5,359,021 | 10/1994 | Weinschenk, III et al. . |
| 5,429,703 | 7/1995 | Hartman et al. . |
| 5,603,774 | 2/1997 | LeBoeuf et al. . |
| 5,674,960 | 10/1997 | Namdaran et al. . |
| 5,932,674 * | 8/1999 | Zhang et al. .......................... 351/161 |
| 5,936,052 * | 8/1999 | Bothe et al. .......................... 526/264 |
| 5,939,466 * | 8/1999 | Bachmann et al. ................... 523/106 |
| 5,965,631 * | 10/1999 | Nicolson et al. ..................... 523/106 |
| 5,994,133 * | 11/1999 | Meijs et al. ........................... 435/395 |
| 5,997,140 * | 12/1999 | Zhang et al. .......................... 351/161 |

FOREIGN PATENT DOCUMENTS

| | | |
|---|---|---|
| 0 514 096 | 11/1992 | (EP) . |
| 95/7751 | 6/1995 | (EP) . |
| 0 811 393 | 12/1997 | (EP) . |
| 94/11764 | 5/1994 | (WO) . |
| 94/25510 | 11/1994 | (WO) . |

* cited by examiner

Primary Examiner—David H. Willse
Assistant Examiner—Hieu Phan
(74) Attorney, Agent, or Firm—Robert J. Baran; Carlos A. Fisher; Martin A. Voet

(57) ABSTRACT

Ophthalmic lenses, such as intraocular lenses, include crosslinked polymeric materials having a first constituent derived from a first monomeric component selected from the group consisting of 2-phenylpropyl acrylate or methacrylate and mixtures thereof, and a second constituent derived from a second component in an amount effective as a crosslinker in the crosslinked polymeric material. The crosslinked polymeric material has branched chain alkyl groups, in an amount effective to reduce the tackiness of the crosslinked polymeric material relative to a substantially identical crosslinked polymeric material without branched chain alkyl groups.

15 Claims, 1 Drawing Sheet

INTRAOCULAR LENSES MADE FROM POLYMERIC COMPOSITIONS AND MONOMERS USEFUL IN SAID COMPOSITIONS

CROSS REFERENCE TO RELATED APPLICATION

This application is a continuation in part of and claims the benefit of U.S. patent application Ser. No. 60/106,381 filed Oct. 29, 1998, and entitled Intraocular Lenses Made From Polymeric Compositions.

BACKGROUND OF THE INVENTION (1) Field of the Invention

The present invention relates to ophthalmic lenses made from polymeric compositions and novel monomers useful in said compositions. More particularly, the invention relates to ophthalmic lenses, preferably deformable intraocular lenses, having reduced surface tackiness made from 2-phenylpropylacrylate and/or methacrylate-based polymeric compositions.

(2) Description of Related Art

Intraocular lenses (IOLs) have been known for a long time, since shortly after the end of World War II. Such a lens is surgically implanted into a mammalian eye, e.g., human eye, to replace a damaged or diseased natural lens of the eye and restore the patient's vision.

Although IOLs are made from "hard" or "rigid" polymeric or glass optical materials, such as polymethyl methacrylate (which has a refractive index of 1.49), soft resilient polymeric materials, such as silicones, have been increasingly used, for the reasons discussed below, in ophthalmic applications.

Since soft IOLs are deformable, for example, foldable or rollable, for implantation, a smaller incision can be surgically cut in the eye than for the implantation of "hard" IOLs of the same optical power. The smaller the incision, the less trauma the patient's eye experiences and the faster post-operative healing occurs. An incision of about 3 mm is ideal since this size incision is presently required to remove the natural lens after it has been broken up, for example, emulsified in a conventional phaceoemulsification procedure. In contrast the typical IOL optic has a diameter of about 6 mm.

The size and mechanical characteristics of the deformable IOLs play an important role. As is well understood by those skilled in the art, for successful implantation, the deformable IOL must have sufficient structural integrity, elasticity and elongation and be small enough in size to permit deforming for insertion through a small incision. After insertion, the lens must, of course, regain its original shape and have sufficient structural integrity to retain such shape under normal use conditions.

In general, the thinner the deformable IOL the smaller the incision in the eye that is required. On the other hand, in order to function optically as an IOL, the lens must have sufficient optical refractory power. Also, the higher the optical refractive index of the material making up the IOL, the thinner the IOL can be and still obtain the same optical refractory power.

Deformable IOLs made of acrylic materials can be quite tacky in nature, which tackiness inhibits deforming to a sufficiently small size for insertion through a very small incision and/or may cause handling problems.

Gupta U.S. Pat. No. 4,834,750 discloses IOLs with optics made of copolymers of methacrylate esters which form homopolymers that are relatively hard at room temperature and acrylate esters which form homopolymers that are relatively soft at room temperature. Such copolymers are crosslinked with a diacrylate ester to produce an acrylate material which preferably includes a constituent derived from a fluoroacrylate to reduce surface tackiness. None of the specific monomers disclosed in this patent provide homopolymers which have a refractive index of at least about 1.50.

Weinschenk, III U.S. Pat. No. 5,331,073 discloses acrylic-based intraocular lenses which optionally include a constituent derived from a hydrophilic monomeric component. This constituent is effective to reduce the tackiness of the copolymer. However, such hydrophilic constituent may cause a disadvantageous decrease in the index of refraction of the final IOL optic in that some water is included within the copolymer.

LeBoeuf et al U.S. Pat. No. 5,603,774 discloses plasma treatment of the polymer surface to reduce tackiness associated with certain acrylic polymers, particularly those polymers useful in intraocular lenses. However, such plasma treatment does involve an additional manufacturing step. Also, the non-homogeneous intraocular lens which results from the surface being treated with plasma has the potential of causing problems in the eye.

Monomers useful in preparing acrylic polymers and co-polymers are well known. For example, see RN 133832-56-1 REGISTRY which discloses homopolymers of 2-propenoic acid, 2-methyl-,2-methyl-3-phenylpropyl ester (s)-, (2-propenoic acid, 2-methyl-3-phenylpropyl ester?) homopolymer.

It would be advantageous to provide ophthalmic lens materials of construction which have good optical properties, including optical clarity and high refractive index (index of refraction) and, in addition, have reduced tackiness without the disadvantages of the prior art materials noted above.

Furthermore, it would be advantageous to provide novel monomers which are useful in the preparation of such ophthalmic lens materials.

BRIEF SUMMARY OF THE INVENTION

New polymeric materials and ophthalmic lenses, for example, IOLs, produced from such polymeric materials have been discovered. The present polymeric materials are derived from 2-phenylpropyl acrylate and/or 2-phenylpropyl methacrylate monomers and provide very useful optical properties in terms of optical clarity and high index of refraction and can be formed into ophthalmic lenses, for example, optics of IOLs which are effectively deformable, preferably foldable, for insertion through small surgical incisions, preferably on the order of about 3 mm or less (in maximum transverse dimension). Importantly, the present compositions and ophthalmic lenses have reduced surface tackiness without requiring the presence of fluoroacrylates, hydrophilic components and without requiring plasma treatment. By selecting the monomeric components used to produce the present compositions and ophthalmic lenses in accordance with the present invention, reduced surface tackiness is achieved with little or no adverse impact on the optical clarity, refractive index, homogeneity, biocompatability, deformability, and cost of production of such compositions and ophthalmic lenses. The present compositions and lenses can be produced using conventional techniques, e.g., conventional polymerization techniques. Thus, the present invention is very effective and easy to practice and results in polymeric compositions and ophthalmic lenses which have outstanding properties.

In one broad aspect of the present invention, ophthalmic lens bodies are provided which comprise crosslinked polymeric materials or compositions. Such materials comprise a first constituent derived from a first monomeric component selected from acrylates, methacrylates and mixtures thereof. Such first constituent will include at least one of 2-phenylpropyl acrylate or 2-phenylpropyl methacrylate as a monomer. A second constituent is included and is derived from a second component in an amount effective as a cross-linker in the crosslinked polymeric material. The resulting crosslinked polymeric material includes 2-phenylpropyl acrylate or 2-phenylpropyl methacrylate in an amount effective to reduce the tackiness of the crosslinked polymeric material relative to a substantially identical crosslinked polymeric material without branched chain alkyl groups. It has been found that the inclusion of 2-phenylpropyl acrylate or 2-phenylpropyl methacrylate, for example, in the first monomeric component, or portion thereof, unexpectedly provides reduced surface tackiness to the crosslinked polymeric material. Thus, this reduced tackiness is obtained without requiring the presence of a fluoroacrylate or a hydrophilic component and without requiring treating, for example, plasma treating, the surface of the polymeric material.

The present ophthalmic lens bodies may be in the form of optics of IOLs, contact lenses, corneal implants (for example, corneal onlays and corneal inlays) and other ophthalmic lens bodies. The present lens bodies are particularly useful as optics of IOLs, more preferably deformable IOLs. Because a deformable IOL is adapted to be deformed, that is rolled, folded or otherwise deformed, prior to insertion into the eye, it is important that the IOL optic have a relatively reduced degree of surface tackiness to provide for effective deforming for insertion and/or to allow the optic to effectively regain its original shape in the eye.

The amount of 2-phenylpropyl acrylate or 2-phenylpropyl methacrylate present is sufficient to provide a crosslinked polymeric material having reduced tackiness relative to a substantially identical crosslinked polymeric material without branched chain alkyl groups. The monomeric component, for example, the first monomeric component, or portion thereof, including 2-phenylpropyl acrylate or 2-phenylpropyl methacrylate used in providing the present crosslinked polymeric materials may represent a wide ranging proportion of the total monomeric components employed. Preferably, the 2-phenylpropyl acrylate or 2-phenylpropyl methacrylate-containing monomeric component, or portion thereof, provides a constituent of the crosslinked polymeric materials which is present in an amount in the range of about 1% or less to about 95% or more, and more preferably about 10% to about 85%, by weight of the crosslinked polymeric material.

In one useful embodiment, the crosslinked polymeric material includes a third constituent derived from a third monomeric component other than the first and second monomeric components. This third monomeric component is selected from acrylates, methacrylates and mixtures thereof. The third monomeric component preferably is selected from acrylates and mixtures thereof.

In one embodiment the present crosslinked polymeric material has reduced tackiness relative to a substantially identical crosslinked polymeric material in which the first constituent is replaced by a constituent derived from a monomeric component having a straight chain alkyl group or phenyl-n-alkyl group having about the same number of carbon atoms as the 2-phenylpropyl acrylate or methacrylate included in the first monomeric component, i.e. an acrylate or methacrylate ester having from about 7 to about 9 carbons in the ester chain, such as, e.g. n-octyl or phenylethyl acrylate or methacrylate monomers.

Advantageously, the crosslinked polymeric material is has an index of refraction of at least about 1.50. Relatively high indexes of refraction allow the ophthalmic lenses, and in particular IOLs, to be conveniently manufactured with relatively high optical powers and the capability of being passed through scleral tunnel incisions of about 3.0 mm or even about 2.8 mm or less. Preferably, the crosslinked polymeric material includes aryl-containing groups from the 2-phenylpropyl acrylate or 2-phenylpropyl methacrylate monomer in an amount effective to increase the index of refraction of the crosslinked polymeric material relative to the index of refraction of a substantially identical crosslinked polymeric material without the aryl-containing groups.

In order to provide the desired degree of deformability, the crosslinked polymeric material preferably has a glass transition temperature (Tg) of about 22° C. or less. Thus, in the context of an IOL optic, a crosslinked polymeric material having a Tg within this preferred range can be folded or otherwise deformed for insertion at or about room temperature.

Each individual feature and each combination of two or more features described herein are included within the scope of the present invention provided that the features included in the combination are not mutually inconsistent.

These and other aspects of the present invention are set forth in the following detailed description, examples and claims, particularly when considered in conjunction with the accompanying drawings in which like parts bear like reference numerals.

DETAILED DESCRIPTION OF THE INVENTION

Figure 1:
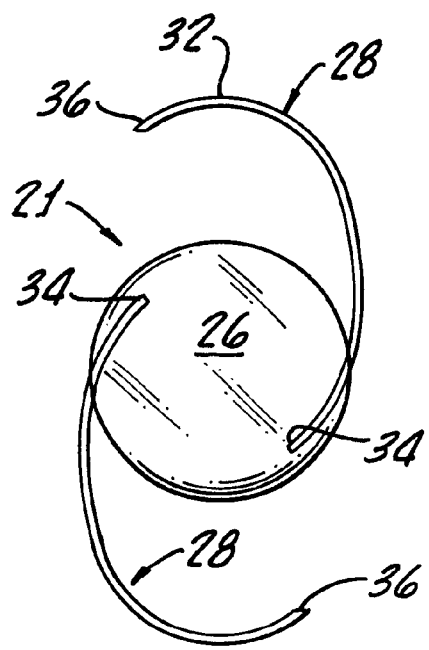
FIG. 1 is a plan view of an IOL in accordance with the present invention.

The present ophthalmic lens bodies comprise crosslinked polymeric materials as described herein. Such crosslinked polymeric materials comprise a combination of constituents derived from different monomeric components. Thus, the present crosslinked polymeric materials comprise a first constituent and a second constituent, and preferably a third constituent.

The first constituent of the present crosslinked polymeric materials is derived from a first monomeric component selected from the group consisting of 2-phenylpropyl acrylate, 2-phenylpropyl methacrylate and mixtures thereof.

The present crosslinked polymeric materials have 2-phenylpropyl acrylate or 2-phenylpropyl methacrylate in an amount effective to reduce the tackiness of the crosslinked polymeric materials relative to a substantially identical crosslinked polymeric materials having a normal alkyl side chains of from about 7 to about 9 carbons or phenyl-n-alkyl side chains of from about 7 to about 9 carbons.

The 2-phenylpropyl acrylate or 2-phenylpropyl methacrylate monomeric component, for example, the first monomeric component, or portion thereof, preferably provides a constituent of the crosslinked polymeric material which is present in an amount in the range of about 1% or less to about 95% or more, more preferably about 3% to about 85% by weight, of the total crosslinked polymeric material.

The homopolymers of 2-phenylpropyl acrylate or 2-phenylpropyl methacrylate have an index of refraction of at least about 1.50, preferably at least about 1.52 or about 1.54.

The second constituent of the present crosslinked polymeric materials is derived from a second monomeric component in an amount effective as a crosslinker in the present crosslinked polymeric materials. This second monomeric component preferably is multi-functional and can chemically react with the first monomeric component, and more preferably with both the first and third monomeric components. The second constituent of the present crosslinked polymeric materials is present in an amount effective to provide a desired degree of shape memory to the materials, for example, to facilitate returning a deformed IOL made from the present crosslinked polymeric material to its original shape, for example, in a reasonable period of time, at the conditions present in the human eye.

The second or crosslinking monomeric component is often present in a minor amount relative to the amounts of the first and third monomeric components. Preferably, the second constituent is present in the crosslinked polymeric material in an amount of less than about 5% by weight of the material. The second constituent of the present crosslinked polymeric materials may be considered to be a crosslinker. The crosslinking monomeric component is often selected from multi functional components, preferably able to chemically react with at least one functional group of each of the first monomeric component and the third monomeric component. The crosslinking monomeric component is chosen to be chemically reactible with at least one functional group associated with one or both of the first monomeric component and the third monomeric component.

Examples of the second monomeric component for use in the present crosslinked polymeric materials include, but are not limited to, ethylene glycol dimethacrylate tetraethylene glycol dimethacrylate, allyl acrylate, ally. methacrylate, trifunctional acrylates, trifunctional methacrylates, tetrafunctional acrylates, tetrafunctional methacrylates and mixtures thereof.

The third monomeric component used in producing the crosslinked polymeric materials of the present invention is different from the first and second monomeric components. Such third monomeric component is selected from acrylates, methacrylates and mixtures thereof. The third constituent of the present crosslinked polymeric materials preferably is present to provide a constituent of the crosslinked polymeric material in an amount of at least about 10% or about 20% by weight, of the crosslinked polymeric material.

In one particularly useful embodiment, the first and third constituents together are preferably at least about 80%, more preferably at least about 95%, by weight of the present crosslinked polymeric materials. The first and third monomeric components preferably are selected so that each of these monomeric components can chemically react with the other monomeric component.

The present crosslinked polymeric materials have reduced surface tackiness and preferably are optically clear and have high indexes of refraction, for example, at least about 1.50, and preferably at least about 1.52 or at least about 1.54. The combination of properties of the present crosslinked polymeric materials, for example, which facilitates the manufacture of effectively deformable IOLs having high optical power, is very advantageous.

As used herein, the term "homopolymer" refers to a polymer which is derived substantially completely from the monomeric component in question. Thus, such homopolymer includes as the primary, preferably sole, monomeric component, the monomeric component in question. Minor amounts of catalysts, initiators and the like may be included, as is conventionally the case, in order to facilitate the formation of the homopolymer. In addition, the homopolymers of both the first monomeric component and the third monomeric component have sufficiently high molecular weights or degrees of polymerization so as to be useful as IOL materials of construction.

The homopolymers of the first monomeric component may be rigid. An IOL made from such a "rigid" homopolymer is not deformable, for example, using systems which are specifically structured and used to deform IOLs for insertion through a small incision into the eye. The rigidity of the homopolymer of the first monomeric constituent may result in an IOL made from such homopolymer being not deformable, or breaking or otherwise deteriorating as a result of the application of force seeking to so deform such IOL for implantation through a small ocular incision.

The first constituent preferably is present in an amount of at least about 10% or at least about 20%, more preferably in a major amount, by weight of the present crosslinked polymeric materials. The third monomeric component from which the third constituent is derived may be selected from compounds which meet the criteria set forth herein for such component. The monomeric component of the first constituent preferably is such as to provide the present crosslinked polymeric materials with increased refractive index relative to the homopolymers of the third monomeric component. The homopolymers of the first monomeric component preferably have an index of refraction of at least about 1.50, and more preferably at least about 1.52 or at least about 1.54.

Without wishing to limit the present invention to any particular theory of operation, it is believed that the presence of aryl-containing groups in the monomers at least facilitates, and preferably leads to or results in, the present crosslinked polymeric materials having desirably high refractive indexes. It is preferred that at least the third monomeric component, and more preferably that the third and second monomeric-components, include no aryl-containing groups. This "single index of refraction control" is very effective in achieving high index of refraction crosslinked polymeric materials, and allows flexibility in selecting the other monomeric component or components so that crosslinked polymeric materials with advantageous properties, other than index of refraction, for example, crosslinked polymeric materials formable into IOLs which can be effectively deformed (for insertion) at room temperature, can be obtained.

Typical examples of the third monomeric component include, but are not limited to n-butylacrylate, n-hexyl acrylate, n-octyl acrylate, n-butyl methacrylate, n-hexyl methacrylate, n-octyl methacrylate, 2-ethylhexyl acrylate, 2-ethylhexyl methacrylate, 2,2-dimethylpropyl acrylate, 2,2-dimethylpropyl methacrylate, trimethylcyclohexyl acrylate, trimethylcyclohexyl methacrylate, isobutyl acrylate, isobutyl methacrylate, isopentyl acrylate, isopentyl methacrylate and mixtures thereof.

More preferably, to further reduce tackiness, the third monomeric component may include a branched chain alkyl ester, e.g. 2-ethylhexyl acrylate, 2-ethylhexyl methacrylate, 2,2-dimethylpropyl acrylate, 2,2-dimethylpropyl methacrylate, trimethylcyclohexyl acrylate, trimethylcyclohexyl methacrylate, isobutyl acrylate, isobutyl methacrylate, isopentyl acrylate, isopentyl methacrylate and mixtures thereof.

Of course, the first, second and third monomeric components should be such as to provide crosslinked polymeric materials which are compatible for use in or on the eye, are optically clear and are otherwise suitable for use as materials of construction for ophthalmic lenses. In one useful embodiment, each of the first, second and third monomeric components is substantially free of silicon, so that the resulting copolymer is not a silicone polymer. The monomeric components may be substituted with substantially non-interfering substituents which have a substantial detrimental effect on the crosslinked polymeric materials produced therefrom. Such substituents may include one or more elements, such as oxygen, nitrogen, carbon, hydrogen, halogen, sulfur, phosphorus, and the like and mixtures and combinations thereof.

The crosslinked polymeric materials of the present invention preferably have glass transition temperatures (Tg) of about 22° C. or less. Such glass transition temperatures (Tg) are beneficial in facilitating the deforming (folding) of an IOL the optic of which is made of an embodiment of the present crosslinked polymeric material at room temperature prior to inserting the IOL through a small incision into the eye.

The present crosslinked polymeric materials may be produced using conventional polymerization techniques. For example, the monomers can be blended together and heated to an elevated temperature to facilitate the polymerization reaction. Catalysts and/or initiators, for example, selected from materials well known for such use in the polymerization art, may be included in the monomer mix in order to promote, and/or increase the rate of, the polymerization reaction. Examples of such initiators include 2,2'-azobis (2,4-dimethylpentanenitrile), 2,2'-azobis (2-methylpropanenitrile), 2,2'-azobis (2-methylbutanenitrile), peroxides such as benzoyl peroxide, UV initiators such as diethoxyacetophenone, and the like and mixtures thereof.

In addition, effective amounts of ultraviolet light absorbing monomeric components, such as functional benzotriazole and benzophenone derivatives, may be included in the precursor monomer mix. Such UV light absorbing monomeric components are polymerized into the final crosslinked polymeric material to provide the final material with effective UV light absorbing properties.

In one particularly useful embodiment, the present crosslinked polymeric materials are produced by mixing together the first monomeric component and the third monomeric component. This mixture is well blended, deareated and heated to a temperature, for example, of about 50° C. to about 80° C. and maintained at this temperature for a period of time, for example, of about 15 minutes to about 3 hours. The mixture undergoes partial polymerization to form a viscous liquid when cooled to about 25° C.

The final crosslinked polymeric materials can be produced by combining this partially polymerized viscous liquid, the second or crosslinking monomeric component and catalyst and/or an initiator. Alternately, all the monomeric components and catalyst and/or initiator can be combined or mixed together. The viscous liquid, or monomeric mixture, is well blended, deareated and poured into a mold. The mold is heated, preferably to a temperature of about 40° C. to about 100° C., and the liquid or mixture is allowed to cure, preferably for about 1 hour to about 24 hours. The material in the mold is then post-cured, preferably at a temperature in the range of about 70° C. to about 130° C., for a period of time, preferably for about 2 to about 30 hours. After curing (and post-curing), the mold is disassembled and the molded lens body recovered.

Alternately, the curing and post-curing occurs in a tube. The crosslinked polymeric material formed in the tube is cut into cylindrical lens blanks. The lens blanks can be machined to produce the finished lens body, e.g., IOL optic. Such machining may involve milling and lathing at cryogenic temperatures.

Figure 2:
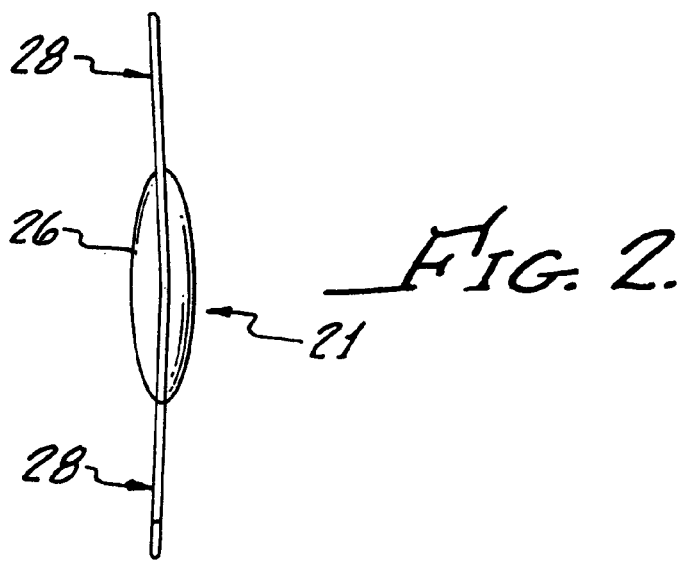
FIG. 2 is a side view of the IOL of FIG. 1.

Referring now to FIGS. 1 and 2, IOL 21 is illustrated as including a pair of radially outwardly extending haptics or fixation members 28 secured to optically clear optic 26. Each haptic 28 has a substantially uniform cross section throughout its length and is shown provided with a smoothly curved region 32, intermediate a lens bonding region 34 and a free end region 36. Although the illustrated embodiment is provided with two opposing haptics 28, it is understood that an IOL having only one haptic or more than two haptics bonded to the optic is within the scope of the invention.

Optic 26 is made of a crosslinked polymeric material in accordance with the present invention, for example, the material as set forth in Example 1 hereof. Optic 26 can be formed in accordance with conventional IOL optic forming techniques, such as by injection molding and the like techniques. Alternately, the monomeric components can be first mixed in a tube and then cured in the tube. The resulting rod then is cut into buttons which are then cryolathed into IOL optics.

Typically, each haptic 28 comprises a flexible member comprising metal or, preferably, polymeric material, and having a substantially circular cross-section, although alternative cross-sectional configurations may be substituted, if desired. Although the haptics may take on any suitable configuration, the illustrated haptics 28 are relatively thin and flexible, while at the same time being sufficiently strong to provide support for IOL 21 in eye 10. The haptics 28 may comprise any of a variety of materials which exhibit sufficient supporting strength and resilience, and which are substantially biologically inert in the intended in vivo environment. Suitable materials for this purpose include, for example, polymeric materials such as polypropylene polyamides, polyimides, polyacrylates, 2-hydroxyethyl methacrylate, poly (vinylidene fluoride), polytetrafluoroethylene and the like; and metals such as stainless steel, platinum, titanium, tantalum, shape-memory alloys, e.g., nitonal, and the like. The haptics can be produced using conventional and well known forming techniques. For example, the preferred polymeric haptics can be formed in accordance with known thermoplastic polymer forming techniques, such as by injection molding or by extrusion.

The lens bonding regions 34 of the haptics 28, which, as described herein, are secured to optic, may be provided with any of a variety of configurations, such as an anchoring loop, an anchoring "T", or other anchor structure, to provide a mechanical interlock with the optic, such as has been done in the prior art.

IOL 26 can be formed using any one of various techniques, such as those conventionally used to form IOLs. For example, the lens bonding regions 34 of haptics 28 can be placed in a mold which is filled with a mix of the monomeric components used to form the optic 26. The mold is then subjected to conditions, e.g., elevated temperature, effective to form the crosslinked polymeric materials of the present invention from this monomer mix. The lens bonding regions 34 become bonded to the optic 26, thereby securing the haptics 28 to the optic. Alternately, the haptics 28 can be secured in recesses provided in the already formed optic 26.

Optic 26 has low or reduced surface tackiness, and preferably an index of refraction of at least about 1.50. Optic 26 is foldable for insertion into a human eye through an incision of about 3 mm in length. After insertion into the eye in the folded condition, IOL 21 returns to its original shape in a reasonable period of time, for example, on the order of about 1 second or about 20 seconds to about three minutes, and can be easily positioned in the eye for effective and long term use as a replacement for the natural lens normally present in the eye.

The following non-limiting examples illustrate certain aspects of the present invention.

EXAMPLE 1

Synthesis of 2-phenylpropyl methacrylate

This monomer is prepared as follows:

A two-mouth one-liter round bottom flask containing a magnetic stir bar is lowered into an ice bath on top of a magnetic stirrer. 25 grams (0.18 mol) of 2-phenyl-1-propanol is added into the flask, followed by the addition of 30 ml (0.22 mol) of triethylamine to the flask. The now empty triethylamine addition flask is rinsed with about 10-ml of anhydrous diethyl ether and this is added to the round bottom flask. Another 200 ml of anhydrous diethyl ether is added to the round bottom flask, followed by 5 mg (0.0002 mol) of inhibitor (2,5-diphenyl-p-benzophenone). The magnetic stirrer stirs the resulting mixture at 555 rpm.

100 ml of anhydrous diethyl ether and 20-ml (0.21 mol) methacryloyl chloride are added, dropwise, while the contents of the flask are maintained at about 2° C. The methacryloyl chloride addition are adjusted so that the addition is completed in about 1 ½ hours. The reaction mix is allowed to continue to stir for about 24 hours and then quenched by adding about 200 ml of distilled water to the reaction mixture. The lower aqueous layer of the quenched mixture is discarded and the remaining organic layer is dried with magnesium sulfate ($MgSO_4$)

The organic solution is decanted and about 5 mg of inhibitor (2,5-diphenyl-p-benzophenone) is added thereto. Another 5 mg of inhibitor (2,5-diphenyl-p-benzophenone), is added along with a few boiling chips, prior to distilling the decanted solution under vacuum (ca. 200 millitorr) while stirring magnetically. The oil bath temperature is raised in stages from 50° C. to 80° C. in order to initially facilitate the removal of solvent. The distillation may take up to 2 hours or more to complete depending upon the vacuum attained.

The first five-ml of distillate that distills at around 60° C. and 200 millitorr is collected. The remainder of the distillate is collected and the final product structure is confirmed by proton NMR analysis.

EXAMPLE 2

Synthesis of 2-phenylpropyl acrylate

The above monomer is prepared as in Example 1 except that acryloyl chloride replaces methacryloyl chloride on an equal molar basis.

EXAMPLE 3

The following formulation is blended, purged with nitrogen for 3 minutes and then cured into a crosslinked copolymer.

|  | Quantity | % Quantity |
|---|---|---|
| 2-phenylpropyl methacrylate | 15.0 g | 33.4% |
| 2-phenylpropyl acrylate | 21.5 g | 47.9% |
| n-hexyl acrylate | 6.5 g | 14.5% |
| EGDMA ethylene glycol dimethacrylate | 0.9 g | 2.0% |
| thermal initiator (2,5-dimethyl-2,5 bis(2-ethylhexanoylperoxy) hexane | 0.1 g | 0.2% |
| UV absorber | 0.9 g | 2.0% |

The resulting crosslinked copolymer has an index of refraction of 1.5396, hardness (Shore A) of 42, haze (after soaking) of 3, excellent optical transparency (clarity) and good mechanical properties, including low or reduced tackiness. A one cm diameter rod of this copolymer is folded 180° with no cracking and returns to its original shape within a few seconds.

EXAMPLE 4

Using conventional techniques, an optic is formed from the crosslinked copolymer produced in Example 3. In order to produce a 20 diopter, plano-convex optic, having a 0.305 mm edge thickness and a 6.0 mm diameter, the optic center thickness is approximately 0.737 mm.

EXAMPLE 5

An IOL is produced having an optic as indicated in Example 4. Two substantially opposing haptics, such as shown in FIGS. 1 and 2, made from extruded poly methyl methacrylate filaments are bonded to this optic. The resulting IOL is inserted into the eye through a 3 mm surgical incision. In order to accomplish such insertion, the IOL is folded. Upon being released into the eye, the IOL regains its original shape in less than one minute and is fixed in position in the eye. After normal healing, the IOL is effective and useful in the eye as a replacement for the natural lens normally present in the eye.

EXAMPLE 6

The crosslinked polymer of Example 3 (Example 3 Copolymer) and a crosslinked copolymer similar to the crosslinked copolymer produced in Example 3 (Example 6 Copolymer) are made or cast in the form of sheets. Both copolymers are made in a manner similar to how the copolymer of Example 3 is made. The composition of the Example 6 Copolymer is similar to the copolymer of Example 3 except that n-nonyl acrylate is used in place of 2-phenylpropyl acrylate or methacrylate.

A series of discs shaped and sized similar to optics of intraocular lenses are produced from each of these sheets. A lens folding forceps is used to fold these discs in half (180°). After holding the folded disc in the forceps for 30 seconds, the disc is released from the forceps into a beaker containing water at 35° C. The amount of time required for the disc to release from itself, referred to as the "tack time", is recorded. Also, the amount of time required of the disc to return to flatness or its original shape, referred to as the "unfold time", is recorded.

Results of these tests demonstrate that the Example 3 Copolymer has reduced tackiness relative to the Example 6

Copolymer. Since substantially the only difference in these two materials is the presence of 2-phenylpropyl acrylate or methacrylate, in the Example 3 Copolymer, these results make clear that this type of monomer is surprisingly effective in advantageously reducing the tackiness of crosslinked copolymers derived from such monomers, and in particular ophthalmic lenses including such copolymers.

While this invention has been described with respect to various specific examples and embodiments, it is to be understood that the invention is not limited thereto and that it can be variously practiced within the scope of the following claims. For example, the IOL may be a disc lens, i.e. no haptics.

What is claimed is:

1. An ophthalmic lens body comprising a crosslinked polymeric material comprising a first constituent derived from a first monomeric component selected from the group consisting of 2-phenylpropyl acrylate or 2-phenylpropyl methacrylate and mixtures thereof, and a second constituent derived from a second monomeric component other than the first monomeric component in an amount effective as a crosslinker in the crosslinked polymeric material.

2. The ophthalmic lens body of claim 1 which is selected from the group consisting of optics of intraocular lenses, contact lenses and corneal implants.

3. The ophthalmic lens body of claim 1 which is a deformable optic of an intraocular lens.

4. The ophthalmic lens body of claim 1 wherein the crosslinked polymeric material includes a third constituent derived from a third monomeric component, other than the first and second monomeric components, selected from the group consisting of acrylates, methacrylates and mixtures thereof.

5. The ophthalmic lens body of claim 1 wherein the crosslinked polymeric material has an index of refraction of at least about 1.50.

6. The ophthalmic lens body of claim 1 wherein the crosslinked polymeric material includes aryl-containing groups in an amount effective to increase the index of refraction of the crosslinked polymeric material relative to the index of refraction of a substantially identical crosslinked polymeric material without the aryl-containing groups.

7. The ophthalmic lens body of claim 1 wherein the crosslinked polymeric material has a glass transition temperature of about 22° C. or less.

8. The ophthalmic lens body of claim 1 which is substantially homogeneous.

9. The ophthalmic lens body of claim 1 wherein the crosslinked polymeric material is substantially free of hydrophilic groups effective to reduce the tackiness of the crosslinked polymeric material.

10. The ophthalmic lens body of claim 1 wherein the second monomeric component is selected from the group consisting of ethylene glycol dimethacrylate, tetraethylene glycol dimethacrylate, alkyl acrylate, alkyl methacrylate, trifunctional acrylates, trifunctional methacrylates, tetrafunctional acrylates, tetrafunctional methacrylates and mixtures thereof.

11. The ophthalmic lens body of claim 5 wherein the third monomeric component is selected from the group consisting of n-butyl acrylate, n-hexyl acrylate, n-octyl acrylate, n-butyl methacrylate, n-hexyl methacrylate, n-octyl methacrylate, 2-ethylhexyl acrylate, 2-ethylhexyl methacrylate, 2,2-dimethylpropyl acrylate, 2,2-dimethylpropyl methacrylate, trimethylcyclohexyl acrylate, trimethylcyclohexyl methacrylate, isobutyl acrylate, isobutyl methacrylate, isopentyl acrylate, isopentyl methacrylate.

12. The ophthalmic lens body of claim 5 wherein the third monomeric component is selected from the group consisting of 2-ethylhexyl acrylate, 2-ethylhexyl methacrylate, 2,2-dimethylpropyl acrylate, 2,2-dimethylpropyl methacrylate, trimethylcyclohexyl acrylate, trimethylcyclohexyl methacrylate, isobutyl acrylate, isobutyl methacrylate, isopentyl acrylate, isopentyl methacrylate.

13. An intraocular lens sized and adapted to be deformed for insertion through an incision into a mammalian eye, the intraocular lens comprising a crosslinked polymeric material comprising a first constituent derived from a first monomeric component selected from the group consisting of 2-phenylpropyl acrylate or 2-phenylpropyl methacrylate and mixtures thereof, a second constituent derived from a second monomeric component other than the first monomeric component in an amount effective as a crosslinker in the crosslinked polymeric material, and a third constituent derived from a third monomeric component, other than the first and second monomeric components, the crosslinked polymeric material having in index of refraction of at least about 1.50 and sufficient 2-phenylpropyl acrylate, 2-phenylpropyl methacrylate or other branched chain alkyl groups in an amount effective to reduce the tackiness of the crosslinked polymeric material relative to a substantially identical crosslinked polymeric material without the branched chain alkyl groups.

14. A monomer suitable for the manufacturing of a lens body for an intraocular lens comprising 2-phenylpropyl acrylate.

15. A monomer suitable for the manufacture of a lens body for an intraocular lens comprising 2-phenylpropyl methacrylate.

* * * * *